United States Patent
Cipolli et al.

[11] Patent Number: 5,314,938
[45] Date of Patent: May 24, 1994

[54] AMELINIC COMPOUNDS AND USE THEREOF IN SELF-EXTINGUISHING POLYMERIC COMPOSITIONS

[75] Inventors: Roberto Cipolli, Novara; Gilberto Nucida, Milan; Enrico Masarati, Piacenza; Roberto Oriani; Mario Pirozzi, both of Milan, all of Italy

[73] Assignee: Ministereo Dell'Universita' E Della Ricerca Scientifica E Technologica, Rome, Italy

[21] Appl. No.: 15,856

[22] Filed: Feb. 10, 1993

Related U.S. Application Data

[62] Division of Ser. No. 756,921, Sep. 9, 1991.

[30] Foreign Application Priority Data

Sep. 11, 1990 [IT] Italy .................. 21420 A/90

[51] Int. Cl.$^5$ .................. C08K 5/3962; C08K 5/357
[52] U.S. Cl. .................. 524/100; 524/83; 524/96; 524/415; 524/416
[58] Field of Search .............. 524/96, 100, 415, 416, 524/83

[56] References Cited

U.S. PATENT DOCUMENTS

| | | | |
|---|---|---|---|
| 4,348,493 | 9/1982 | Loffelman | 544/198 |
| 4,400,505 | 8/1983 | Loffelman et al. | 544/198 |
| 4,547,548 | 10/1985 | Cantatore | 544/198 |
| 4,629,752 | 12/1986 | Layer et al. | 544/198 |
| 4,639,479 | 1/1987 | Lai et al. | 544/198 |
| 4,691,015 | 9/1987 | Behrens et al. | 544/198 |
| 5,019,613 | 5/1991 | Ravichandran et al. | 544/198 |
| 5,104,986 | 4/1992 | Cipolli et al. | 544/198 |

*Primary Examiner*—Kriellion S. Morgan
*Attorney, Agent, or Firm*—Oblon, Spivak, McClelland, Maier & Neustadt

[57] ABSTRACT

Amelinic compounds of general formula (I)

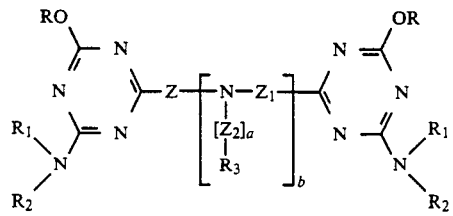

obtained by subsequent condensation reaction of 1 mol of a cyanuric acid halide with 1 mol of amine and of a polyamine and by hydrolysis reaction of the thus obtained intermediate. Compounds of general formula (I) are used, in particular, as antiflame additives.

14 Claims, No Drawings

AMELINIC COMPOUNDS AND USE THEREOF IN SELF-EXTINGUISHING POLYMERIC COMPOSITIONS

This is a division of application Ser. No. 07/756,921, filed on Sep. 9, 1991.

BACKGROUND OF THE INVENTION

1. Field of the Invention

The present invention relates to polycondensation compounds derived from 2,4-diamino-6-hydroxy-1,3,5-triazine (ameline).

More particularly the present invention relates to ameline derivatives and to the use thereof for the preparation of self-extinguishing polymeric compositions, based on thermoplastic polymers or polymers endowed with elastomeric properties, expecially olefinic polymers and copolymers, in combination with phosphates and/or phosphonates of ammonium or of amine.

2. Discussion of the Background

There are various solutions known in the art to reduce or to remove the combustibility of polymers. Some of these solutions are based on the use of metal compounds, especially antimony, bismuth or arsenic, in combination with organic compounds that are partially halogenated and thermally unstable, such as chlorinated paraffinic waxes.

Other solutions are based on the use of substances able to produce intumescence. Formulations of the intumescent type generally consist of the polymer and of at least three main additives: one essentially phosphorated, the purpose of which is to form, on combustion, an impermeable, semi-solid, vitreous layer, essentially consisting of polyphosphoric acid, and to activate the process for the formation of the intumescence; a second containing nitrogen which acts as foaming agent; and a third one containing carbon which acts as carbon donor for the formation of an insulating cellular carbon layer (char) between the polymer and the flame.

Examples of intumescent formulations of this type are those described in U.S. Pat. No. 3,810,862 (Phillips Petroleum Co.) based on melamine, pentaerythritol and ammonium polyphosphate, U.S. Pat. No. 4,727,102 (Vamp s.r.l.) consisting of isocyanuric acid and ammonium polyphosphate, and in the published patent appln. WO 85/05626 (Plascoat U.K. Limited) consisting of several phosphorus and nitrogen compounds, among which, in particular, are a combination of melamine phosphate, pentaerythritol and ammonium polyphosphate.

More recent formulations have used, together with an organic or inorganic phosphorous compound, an organic compound containing nitrogen, generally an aminoplastic resin obtained by condensing urea, melamine or dicyanodiamide with formaldehyde.

Examples of formulations consisting of two additives are those reported in U.S. Pat. No. 4,504,610 (Montedison S.p.A.), based on oligomeric derivatives of 1,3,5-triazine and ammonium polyphosphate, and European Pat. 14.463 (Montedison S.p.A.), based on organic compounds selected from benzylguanamine and reaction products between aldehydes and several nitrogenous cyclic compounds, in particular benzylguanamine-formaldehyde copolymers, and ammonium polyphosphate.

It is also possible to obtain self-extinguishing compositions using monocomponent additives, containing in the organic molecule both nitrogen and phosphorus, as described in U.S. Pat. No. 4,201,705 (Borg-Warner Corp.).

These intumescent retarding systems give to the polymer containing them the property of forming a carbon residue as a result of a fire or application of a flame. Retarder systems of this type show many advantages: absence of corrosion phenomena in apparatus in which polymers are processed, lower emission of smoke in comparison with systems containing metal compounds and halogenated hydrocarbons, and overall the possibility of giving satisfactory antiflame properties to polymers, using a lower amount of additive and therefore without an excessive decay of mechanical properties of polymers themselves.

SUMMARY OF THE INVENTION

It has now been discovered that it is possible to give high antiflame properties to polymers by using a class of polycondensed compounds derived from 2,4-diamino-6-hydroxy1,3,5-triazine, which are more effective than products known in the art.

Furthermore, the new additives exhibit a good heat stability, while maintaining a high activity of flame retardation due to the heat working processes of the polymeric compositions containing them.

Still further, polymeric compositions formulated with products of the present invention have the advantage of giving rise, in the event of fire, to a very low emission of, and non-darkening, fumes.

Therefore, one object of the present invention is to provide amelinic compounds of general formula (I):

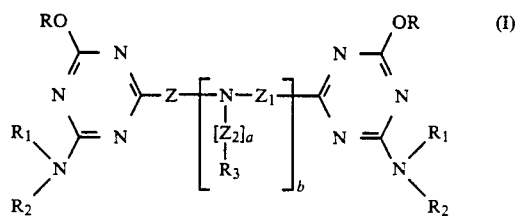

wherein
R = H; $\text{---}C_nH_{2n}\text{---}Y$ wherein
n is an integer comprised between 1 and 8, preferably between 1 and 4;
Y is H; CN; —O—($C_1$–$C_4$)-alkyl; —O—($C_2$–$C_4$)-alkenyl; ($C_6$–$C_{12}$)-cycloalkyl or alkylcycloalkyl; —O—($C_6$–$C_{12}$)-aryl,

wherein radicals $R_4$, which can be the same or different, are: ($C_1$–$C_4$)-alkyl or ($C_3$–$C_4$)-alkenyl; or the group:

is replaced by a heterocylic radical bound to the alkyl chain through the nitrogen atom and optionally containing another heteroatom preferably selected from O, S, N; $(C_2-C_6)$-alkenyl; $(C_6-C_{12})$-cycloalkyl or alkylcycloalkyl; $(C_6-C_{12})$-aryl or -aralkyl;

radicals $R_1$ and $R_2$, which can be the same or different, and which can have different meanings on each triazine ring, are:

H; $(C_1-C_{18})$-alkyl; $(C_2-C_8)$-alkenyl; $(C_6-C_{16})$-cycloalkyl or -alkylcycloalkyl;

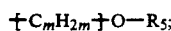

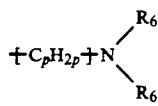

with:

m = integer comprised between 2 and 8, preferably between 2 and 4;
p = integer comprised between 2 and 6;
$R_5$ = H; $(C_1-C_8)$-alkyl, preferably H or $(C_1-C_4)$-alkyl; $(C_2-C_6)$-alkenyl;

$+C_qH_{2q}+O-R_7$ wherein q is an integer comprised between 1 and 4 and $R_7$ is H or an $(C_1-C_4)$-alkyl; $(C_6-C_{12})$-cycloalkyl or -alkylcycloalkyl;

radicals $R_6$, which can be the same or different, are:

H; $(C_1-C_8)$-alkyl; $(C_2-C_6)$-alkenyl; $(C_6-C_{12})$-cycloalkyl or alkylcycloalkyl; $(C_1-C_4)$-hydroxyalkyl or the group:

is replaced by a heterocyclic radical bound to the alkyl chain through the nitrogen atom and optionally containing another heteroatom preferably selected from O, S, N; or in the general formula (I) the group:

is replaced by a heterocyclic radical bound to the triazinic ring through the nitrogen atom and optionally containing another heteroatom preferably selected from O, S, N;

a is 0 or 1;
b is 0 or an integer comprised between 1 and 5;
$R_3$ is hydrogen or:

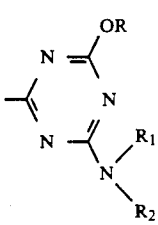

and its meaning may vary within each repeating unit;

when b is O, Z is a divalent radical comprised in one of the following formulas:

wherein radicals $R_8$, which can be the same or different, are hydrogen or $(C_1-C_4)$-alkyl;

wherein r is an integer comprised between 2 and 14; $R_9$ is hydrogen; $(C_1-C_4)$-alkyl; $(C_2-C_6)$-alkenyl; $(C_1-C_4)$-hydroxyalkyl;

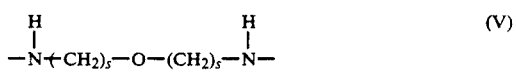

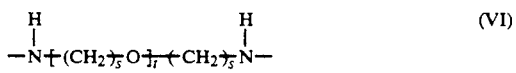

wherein s is an integer comprised between 2 and 5 and t is an integer comprised between 1 and 3;

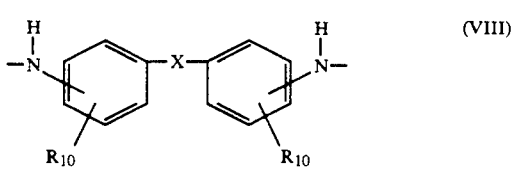

wherein:
X is a direct bond C—C; O; S; S—S; SO; $SO_2$; NH; $NHSO_2$; NHCO; N=N; $CH_2$;
$R_{10}$ is hydrogen; hydroxyl; $(C_1-C_4)$-alkyl; $(C_1-C_4)$-alkoxy;

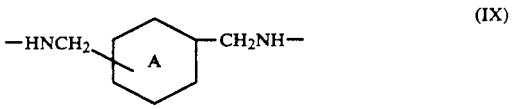

wherein A may be either a saturated or an unsaturated ring;

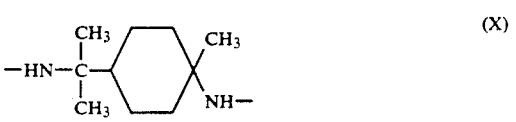

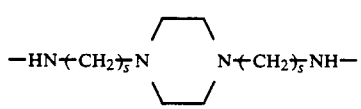

wherein s has the previously defined meaning;
when b is on the contrary an integer comprised between 1 and 5, the group:

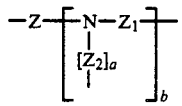

is a polyvalent radical comprised in one of the following formulas:

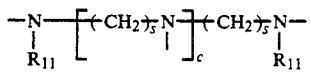

wherein:
$R_{11}$ is hydrogen or $(C_1-C_4)$-alkyl;
c is an integer comprised between 1 and 5;
indexes s, which can be the same or different, have the previously defined meaning;

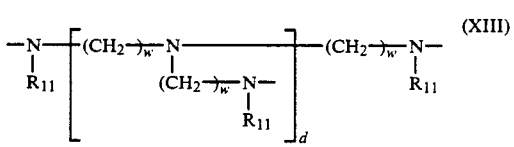

wherein:
$R_{11}$ has the previously defined meaning;
w is an integer comprised between 2 and 4;
d is 1 or 2.

To the general formula (I) also belong those derivatives having an asymmetric structure, in that radicals R and $R_1$ may have a different meaning on each triazinic ring.

Examples of radical R in the general formula (I) are: methyl; ethyl; propyl; isopropyl; n-butyl; isobutyl; ter-butyl; n-pentyl; isopentyl; n-hexyl; ter-hexyl; octyl; ter-octyl; ethenyl; propenyl; butenyl; isobutenyl; hexenyl; cyclohexyl; propylcyclohexyl; butylcyclohexyl; phenyl; benzyl; 2-phenylethyl; cyanomethyl; 2-cyanoethyl; 2-methoxyethyl; 2-methoxypropyl; 4-methoxybutyl; 5-methoxypentyl; 6-methoxyhexyl; 7-methoxyheptyl; 7-methoxyoctyl; 2-ethoxyethyl; 3-ethoxypropyl; 4-ethoxybutyl; 5-ethoxypentyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-phenoxyethyl; 2-(N,N-dimethylamino)ethyl; 3-(N,N-dimethylamino)propyl; 4-(N,N-dimethylamino)butyl; 5-(N,N-dimethylaminopentyl; 6-(N,N-dimethylaminohexyl; 4-(N,N-diethylamino)butyl; 5-(N,N-diethylamino)pentyl; 2-(N,N-dipropylamino)ethyl; 4-(N,N-dipropylamino)butyl; 2-(N,N-diisopropylamino)ethyl; 2-(N-methyl-N-1-propenylamino)ethyl; 2-(N,N-di 1-propenylamino)ethyl; 4-(N,N-di-1-propenylamino)butyl; etc.

Examples of radicals $R_1$ and $R_2$ are: methyl; ethyl; propyl; isopropyl; n-butyl; isobutyl; ter-butyl; n-pentyl; isopentyl; n-hexyl; ter-hexyl; octyl; ter-octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxypropyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino) ethyl; 3-(N,N-dimethylamino)propyl; 4-(N,N-dimethylamino)butyl; 5-(N,N-dimethylamino)pentyl; 4-(N,N-diethylamino)butyl; 5-N,N-diethylamino)pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; etc.

Examples of heterocyclic radicals which may replace the group:

in the general formula (I) are:
aziridine, pyrrolidine, piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; etc.

Examples of heterocyclic radicals which can replace the group:

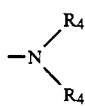

are:
pyrrolidine; piperidine; morpholine; thiomorpholine; piperazine; 4-methylpiperazine; 4-ethylpiperazine; etc.

Examples of heterocyclic radicals which can replace the group:

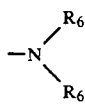

are:
aziridine; pyrrolidine; piperidine; morpholine; thiomorphone; piperazine; 4-methylpiperazine; 4-ethylpiperazine; etc.

Examples of divalent radicals —Z— are those derived by removing a hydrogen from each amino group from the following diamino compounds: piperazine; 2-methylpiperazine; 2,5-dimethylpiperazine; 2,3,5,6-tetramethylpiperazine; 2-ethylpiperazine; 2,5-diethylpiperazine; 1,2-diaminoethane; 1,3-diaminopropane; 1,4-diaminobutane; 1,5-diaminopentane; 1,6-diaminohexane; 1,8-diaminooctane; 1,10-diaminodecane; 1,12-diaminododecane; N,N'-dimethyl-1,2-diaminoethane; N-methyl-1,3-diaminopropane; N-ethyl-1,2-diaminoethane; N-isopropyl-1,2-diaminoethane; N-(2-hydroxyethyl)-1,2-diaminoethane; N,N'bis(2-hydroxyethyl)-1,2-diaminoethane; N-(2-hydroxyethyl)-1,3-diaminopropane; N-hexenyl-1,6-diaminohexane; N,N'-diethyl-1,4-diamino-2-butene; 2,5-diamino-3-hexene; 2-aminoethylether; (2-aminoethoxy) methylether; 1,2-bis(2-aminoethoxy)ethane; 1,3-diaminobenzene; 1,4-diaminobenzene; 2,4-diaminotoluene; 2,4-diaminoanisole; 2,4-diaminophenol; 4-aminophenylether; 4,4'-methylendianiline; 4,4'-diaminobenzanilide; 3-aminophenylsulfone; 4-aminophenylsulphone; 4-aminophenylsulfoxide; 4-aminophenyldisulfide; 1,3-bis(aminomethyl)benzene; 1,4-bis(aminomethyl)benzene; 1,3-bis(aminomethyl)cyclohexane; 1,8-diamino-p-methane; 1,4-bis(2-aminoethyl)piperazine; 1,4-bis(3-aminopropyl)piperazine; 1,4-bis(4-aminobutyl)piperazine; 1,4-bis(5-aminopentyl)piperazine; etc.

Examples of polyvalent radicals

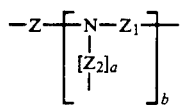

are those derived, by removing a hydrogen from each reacted amino group, from the following polyamino compounds: bis(2-aminoethyl)amine; bis(3-aminopropyl)amine; bis(4-aminobutyl)amine; bis(5-aminopentyl)amine; bis[2-(N-methylamino)ethyl]amine; 2-N-butylbis(2-aminoethyl) amine; bis[3-(N-methylamino)propyl]amine; N-(3-aminopropyl)-1,4-diaminobutane; N-(3-aminopropyl)-1,5-diaminopentane; N-(4-aminobutyl)-1,5-diaminopentane; tris(2-aminoethyl)amine; tris(3-aminopropyl)amine; tris(4-aminobutyl)amine; tris[2-(N-ethylamino)ethyl]amine; N,N'-bis(2-aminoethyl)-1,2-diaminoethane; N,N'-bis[3-(aminopropyl)-1,3-diaminopropane; N,N'-bis(2-aminoethyl)-1,3-diaminopropane; N,N'-bis-(3-aminopropyl)-1,2-diaminoethane; N,N'-bis(3-aminopropyl)-1,4-diaminobutane; bis[2-(2-aminoethyl)aminoethyl]amine; N,N'-bis[2-(2-aminoethyl)aminoethyl]-1,2-diaminoethane; N,N'-bis-[3-(2-aminoethyl)aminopropyl]-1,2-diaminoethane; N,N,N',N'-tetrakis(2-aminoethyl)-1,2-diaminoethane; etc.

Specific compounds comprised in the general formula (I) are reported in examples following the present description and in Table 1.

Compounds of general formula (I) can be prepared from the intermediates of general formula (XIV):

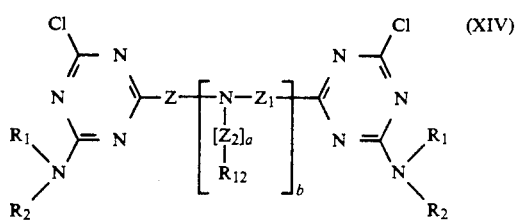

wherein substituents $R_1$ and $R_2$, the radical:

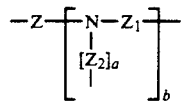

have the previously defined meaning and $R_{12}$ is hydrogen or:

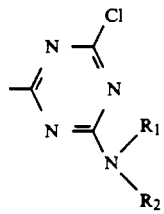

and its meaning may vary within each repeating unit, according to the following modalities:

a) when R is hydrogen by hydrolysis reaction either with an acid (such as for instance, hydrochloric acid, hydrobromic acid, sulfuric acid, phosphoric acid, etc.) at temperatures comprised between 60° and 100° C. or with a base (such as for instance sodium hydroxide, potassium hydroxide, etc.) at temperatures comprised between 100° and 180° C.;

b) when R is different from hydrogen by condensation reaction with a reagent of general formula (XV):

R—OH    (XV)

wherein R has the previously defined meaning, in a suitable solvent (such as for instance toluene, xylene, ortho-dichlorobenzene, etc.) or in excess of reagent (XV) in the event that it can act as solvent (such as for instance methyl alcohol, ethyl alcohol, etc.) in the presence of a base (such as for instance, sodium hydroxide, potassium hydroxide, metal sodium, etc.) at temperatures comprised between 60° and 150° C.

The product formed can be easily separated from the reaction mass by filtration

Generally, products of general formula (I) are obtained showing good quality, in form of white, crystalline powder, useable in self-extinguishing polymeric compositions without any further purification Intermediates of general formula (XIV) can be easily synthetized by allowing to react at temperatures comprised between 0° and 10° C. and at a pH comprised between 5 and 7, a number of mols lower than or equal to (2+b) of a cyanuric acid halide, for instance the chloride, in a suitable solvent (such as for instance acetone, water, methylene chloride, etc.) with one mol of polyamine of the general formula (XVI):

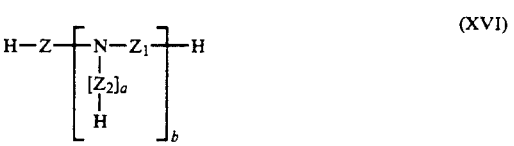

corresponding to one of the structures comprised in general formulas from (II) to (XIII) to give the intermediate of general formula (XVII):

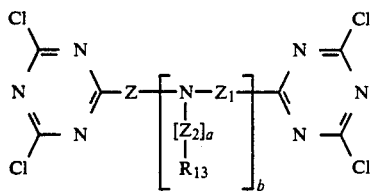

where R₁₃ is hydrogen or:

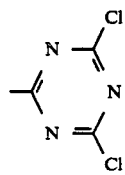

and its meaning can vary within each repeating unit.

This intermediate, either separated or not, is allowed to react again with a number of mols lower than or equal to (2+b) of an amine of the general formula (XVIII):

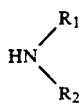

wherein $R_1$ and $R_2$ have the previously defined meanings, under conditions analogous to the preceding ones, but at temperatures comprised between 10° and 60° C.

Obviously, a synthetic variant consists in inverting the order of addition of reagents, that is, in allowing to react at first a cyanuric acid halide, for instance the chloride, under conditions analogous to the preceding ones, at temperatures comprised between 0° and 10° C., with an amine of general formula (XVIII) to give the intermediate of general formula (XIX):

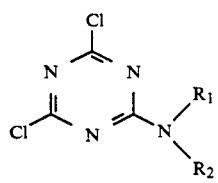

which, either separated or not, is then allowed to react, in number of mols lower than or equal to (2+b) with one mol of a polyamine of general formula (XVI), under conditions analogous to the preceding ones, but at temperatures comprised between 10° and 60° C.

An alternative method to obtain compounds of general formula (I) wherein R is different from hydrogen, consists in allowing to react a cyanuric acid halide, for instance the chloride, with a reagent of general formula (XV), at temperatures comprised between 10° and 110° C., in a suitable solvent (such as for instance acetone, methylene chloride, toluene, xylene, etc.) or in excess of the reactive itself if it can act as solvent (such as for instance methyl alcohol, ethyl alcohol, etc;) in the presence of an acidity acceptor (such as for instance NaHCO₃, NaOH, Na₂CO₃, triethylamine, collidine, etc.) thus obtaining the intermediate of general formula (XX):

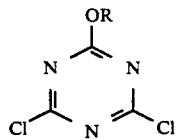

wherein R has the previously defined meaning.

This intermediate, either separated or not, is allowed to react with an amine of general formula (XVIII) under conditions analogous to the preceding ones, but at temperatures comprised between −5° and 30° C., to give the intermediate of general formula (XXI):

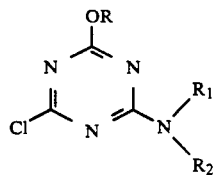

wherein R, $R_1$ and $R_2$ have the previously defined meanings

This intermediate, either separated or not, is then reacted in an amount lower than or equal to (2+b) moles per mol of a polyamine of general formula (XVI), under conditions analogous to the preceding ones, but working at temperatures comprised between 40° and 140° C.

From compounds of general formula (I) wherein R is different from hydrogen, preferably a ($C_1$-$C_4$)-alkyl, it is possible to obtain the corresponding compounds wherein R is hydrogen by hydrolysis reaction, either with an acid by working at temperatures comprised between 80° and 140° C., or with a base by working at temperatures comprised between 100° and 180° C., using the same reactives indicated for the hydrolysis of intermediates of general formula (XIV).

Furthermore, another object of the present invention are self-extinguishing polymeric compositions comprising:

a) from 90 to 40 parts by weight of a thermoplastic polymer or of a polymer endowed with elastomeric properties;

b) from 6 to 33, preferably from 8 to 30, parts by weight of one or more phosphates and/or phosphonates of ammonium or of amine;

c) from 3 to 27, preferably from 4 to 20 parts, by weight of one or more polycondensed compounds derived from 2,4-diamino-6-hydroxy-1,3,5-triazine, of general formula (I):

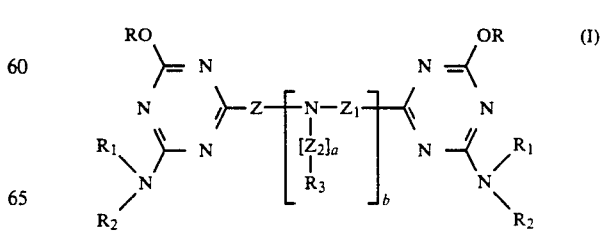

wherein substituents from R to $R_3$ and the group:

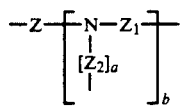

have the previously defined meaning.

Particularly preferred are compounds of general formula (I) wherein R is hydrogen Among phosphates, ammonium polyphosphates of the general formula $(NH_4)_{n+2}P_nO_{3a+1}$, wherein n represents an integer equal to or higher than 2, are preferred; preferably the molecular weight of polyphosphates is high enough to secure a low water solubility As an example, n varies preferably from 2 to 500.

The composition of polyphosphates having the above specified formula, wherein n is a number high enough and preferably comprised between 5 and 500, is, practically-speaking, that corresponding to the formula of methaphosphates $(NH_4PO_3)_n$.

An example of these polyphosphates is that known under the trade name "Exolit 422" (manufactured and sold by Hoechst), having the composition $(NH_4PO_3)_n$, wherein n is higher than 50; another example is the product known under the trade mark "Phos-Chek P/30" (Monsanto Chemical), having an analogous composition Another polyphosphate advantageously useable, in particular owing to a reduced solubility in water, is that known under the trade name "Exolit 462" (produced and sold by Hoechst), corresponding to Exolit 422 microincapsulated in melamine-formaldehyde resin.

Other phosphates useable are those derived from amines, such as for instance dimethylammonium or diethylammonium phosphate, ethylenediamine phosphate, ortho- or pyrophosphate of melamine Among phosphonates, very good results have been obtained using ammonium phosphonates (mono or poly substituted) derived from mono or polyphosphonic acids, examples of which are: ethane-1,1,2-triphosphonic acid; 2-hydroxyethane-1,1,2-triphosphonic acid; propane-1,2,3-triphosphonic acid; methylphosphonic acid; ethylphosphonic acid; n-propylphosphonic acid; n-butylphosphonic acid; phenylphosphonic acid; 1-aminoethane-1,1-diphosphonic acid; 1-hydroxyethane-1,1-diphosphonic acid; 1-hydroxydodecane-1,1-diphosphonic acid; phosphonoacetic acid; 2-phosphonopropionic acid; 3-phosphonopropionic acid; 2-phosphonobutyric acid; 4-phosphonobutyric acid; aminotris(methylenephosphonic) acid; ethylenediaminotetra(methylenephosphonic) acid; hexamethylenediaminotetra(methylenephosphonic) acid; diethylenetriaminopenta(methylenephosphonic) acid; etc.

Among polymers useable in compositions of the present invention there are preferred olefin polymers or copolymers of general formula $R-CH=CH_2$ wherein R is a hydrogen atom or a $(C_1-C_8)$-alkyl or -aryl radical, in particular:

1. isotactic or prevailingly isotactic polypropylene;
2. HDPE, LLDPE, LDPE polyethylene;
3. crystalline copolymers of propylene with a lower proportion of ethylene and/or other alpha-olefins, such as for instance 1-butene; 1-hexane; 1-octene; 4-methyl-1-pentene;
4. heterophasic compositions comprising: (A) a homopolymeric fraction of propylene or one of copolymers specified under item (3), and (B) a copolymeric fraction formed from elastomeric copolymers of ethylene with an alpha-olefin, optionally containing lower proportions of a diene, wherein the alpha-olefin is preferably selected from propylene and butene-1;
5. elastomeric copolymers of ethylene with alpha-olefins optionally containing a lower proportion of a diene. Examples of dienes that are among those more commonly present in the above mentioned elastomeric copolymers are butadiene, ethylidene-norbornene, and 1,4-hexadiene Among olefin polymers of formula $R-CH=CH_2$ wherein R is an aryl radical, "crystal" polystyrene and antishock polystyrene are preferred.

Other examples of commonly useable polymers are acrylonitrile/butadiene/styrene (ABS) copolymers and styrene/acrylonitrile (SAN) copolymers; polyurethane (polyester and polyether); polyethyleneterephthalate; polybutyleneterephthalate; polyamides; etc.

Self-extinguishing compositions of the present invention can be prepared according to known methods: for instance the phosphate and/or the phosphonate of ammonium or of amine is first intimately mixed with one or more nitrogenous compounds of general formula (I) finely milled (preferably with particles lower than 70 microns) and the thus obtained mixture is added to the polymer in a turbomixer to give a homogeneous blend which is extruded and granulated. The granulated product thus obtained can be transformed into several manufactured articles according to any one of known molding techniques.

Antiflame additives of the present invention can be used also in the field of antifire paints Amelinic compounds comprised in the general formula (I), not mentioned in examples, but equally advantageously useable in self-extinguishing polymeric compositions that are the object of the present invention are those reported in the following Table 1, wherein $R_3$, when present, is replaced by the triazinic ring of formula:

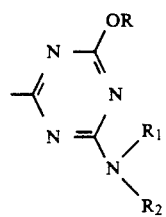

TABLE 1

| Products | R | $R_1-N-R_2$ | | $-Z-\left[N-Z_1\right]_b$ $[Z_2]_a$ |
|---|---|---|---|---|
| 1 | $C_2H_5$ | $CH_2CH_2N(CH_3)_2$ | H | piperazine: $-N\underset{\smile}{\frown}N-$ |
| 2 | $CH_2CH_2N\langle CH_2CH_2\rangle$ (pyrrolidinyl-CH$_2$) | $CH_2CH_2OH$ | $CH_3$ | $-HN-CH_2CH_2-NH-$ |
| 3 | $CH_3$ | morpholino $-N\langle O\rangle$ | | $-N-CH_2-CH=CH-CH_2-N-$ <br> $\;\;\;\;\;\;\;\;C_2H_5\;\;\;\;\;\;\;\;\;\;\;\;\;\;\;\;\;\;\;\;\;\;\;\;C_2H_5$ |
| 4 | H | $(CH_2)_4OCH_3$ | H | $-HN-(CH_2)_4-N-(CH_2)_3-NH-$ <br> $\;\;\;\;\;\;\;\;\;\;\;\;\;\;\;\;\;\;\;\;\;\;\;\;\;\|$ |
| 5 | $CH_2CH_2N(CH_3)_2$ | morpholino | | $-HN-(CH_2)_4-NH-$ |
| 6 | H | $CH_2-C(CH_3)=CH_2$ | | $-HN-(CH_2)_3N(H)-(CH_2)_2N(H)-(CH_2)_3NH-$ |
| 7 | H | $CH_2CH_2CH_2N\langle piperidinyl\rangle$ | H | $-HN-(CH_2)_6NH-$ |
| 8 | $CH_2$-phenyl | H | H | 2,5-dimethylpiperazinyl: $-N\langle CH(CH_3)CH_2\rangle N-$ with $CH_3$ groups |
| 9 | $CH_2CH_2OCH_3$ | morpholino | | $-N-CH_2CH_2-N-$ <br> $\;\;CH_2CH_2OH\;\;\;\;CH_2CH_2OH$ |
| 10 | H | morpholino | | $-HNCH_2CH_2OCH_2CH_2NH-$ |
| 11 | H | $CH_2CH_2OH$ | H | $-HNCH_2-\langle cyclohexyl\rangle-CH_2NH-$ |
| 12 | cyclohexyl | $(CH_2)_3OH$ | H | $-HN-CH_2CH_2-NH-$ |

TABLE 1-continued

| Products | R | $R_1$—N—$R_2$ | | $-Z-\left[\begin{array}{c}N-Z_1\\ |\\ [Z_2]_a\\ |\end{array}\right]_b$ |
|---|---|---|---|---|
| 13 | $CH_2CH_2CN$ | H | H | —N⟨  ⟩N— (piperazine) |
| 14 | $CH_2CH_2O—$ | $(CH_2)_3OC_2H_5$ | H | —HN—$(CH_2)_6$—NH— |
| 15 | $(CH_2)_3N(C_2H_5)_2$ | H | H | —N⟨  ⟩N— (piperazine) |
| 16 | H | $CH_2\underset{OH}{\overset{|}{C}HCH_3}$ | H | $-\underset{CH_3}{\overset{|}{N}}-CH_2CH_2-\underset{CH_3}{\overset{|}{N}}-$ |

The following examples illustrate the characteristics of the invention without limiting them.

EXAMPLE 1

Into a 2 liter reactor, equipped with stirrer, thermometer, feeding funnel, condenser and cooling bath, 600 cc of acetone and 184.5 g of the cyanuric acid chloride are introduced.

While cooling from the outside to the temperature of 0°-5° C., 42.6 g of piperazine dissolved in 400 cc of acetone are added within one hour.

Always at 0°-5° C. 40 g of sodium hydroxide in 200 cc of water are added within about 2 hours.

The whole is kept under agitation for further 4 hours at 5° C., then 400 cc of cold water are added and the formed precipitate is filtered and washed on the filter with water.

After drying of the cake in oven at 100° C., 177.4 g of the intermediate (XXII):

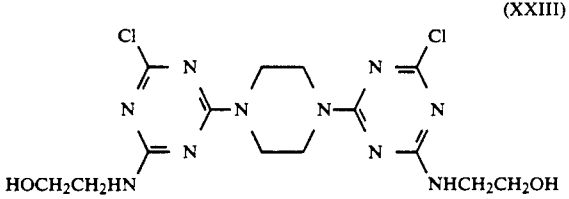
(XXII)

are obtained in form of white crystalline powder, having m.p. higher than 300° C. (m.p.=melting point) and chlorine content equal to 37.35% (theor.: 37.17%).

In the same 2 liters reactor, but equipped with heating bath, 800 cc of xylene and 152.8 g of the intermediate (XXII) are introduced.

The mixture is heated to the temperature of 50° C. and thereafter within 4 hours 48.8 g of 2-hydroxyethylamine are first added, followed by 32 g of sodium hydroxide in 100 cc of water.

The whole is kept under agitation at 50°-55° C. for further 4 hours, and then cooled to room temperature. The product formed is filtered and washed on the filter with copious amounts of water.

After drying of the cake in oven at 100° C., 146.7 g of the intermediate (XXIII):

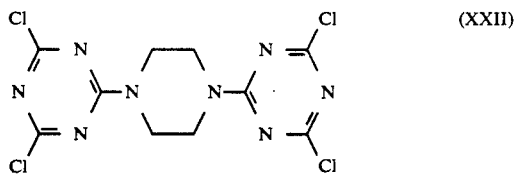
(XXIII)

are obtained in form of white crystalline powder having a m.p. higher than 300° C. and chlorine content equal to 16.62% (theor.: 16.47%).

The structure of intermediates (XXII) and (XXIII) has been confirmed by the IR spectroscopic analysis.

In a 1 liter reactor, equipped as the preceding one, 500 cc of water, 86.2 g of the intermediate (XXIII) and 79.0 g of a 37% by weight hydrochloric acid solution are introduced.

The mass is heated at 95° C. and is kept for 6 hours at this temperature.

Thereafter the mass is cooled to 80° C. and 40 g of sodium hydroxide dissolved in 100 cc of water are added.

The whole is allowed to cool to room temperature and the product formed is filtered and washed on the filter with water.

By drying the cake in oven at 100° C., 70.2 g of the product:

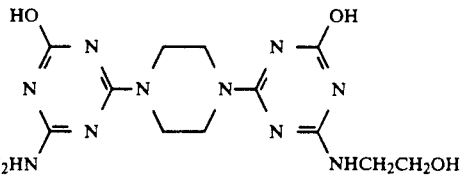

are obtained in form of white crystalline powder having m.p. higher than 300° C.

EXAMPLE 2

In the same 2 liter reactor of example 1, 500 cc of acetone and 300 cc of water are introduced.

After having cooled to 0°–5° C., 92.2 g of the cyanuric acid chloride are introduced and thereafter, within 2 hours, by keeping the temperature at 3°–5° C., 15 g of ethylenediamine dissolved in 100 cc of water are fed.

The mixture is kept for further one hour at 5° C. and then, within one hour, keeping the temperature at 5°–7° C., 42 g of sodium bicarbonate are introduced. The whole is kept under agitation at 7°–10° C. for 2 hours and then the mass is heated at 35° and at this temperature, within one hour, 37.5 g of 2-methoxyethylamine dissolved in 100 cc of water are fed.

The temperature is raised again to 40°–45° C. and within 2 hours 20 g of sodium hydroxide dissolved in 50 cc of water are added. After having kept the whole under agitation one hour more, the acetone is distilled off.

The mass is subsequently heated at 80° C. and 54.2 g of a 37% by weight hydrochloric acid solution are introduced.

The whole is heated to boiling and is maintained under reflux for 6 hours.

Thereafter the whole is cooled to 80° C. and 42 g of sodium hydroxide dissolved in 100 cc of water are introduced.

After having allowed to cool to 50° C., the product formed is filtered and washed on the filter with water at 50°.

By drying the cake in oven at 100° C., 71.5 g of the product:

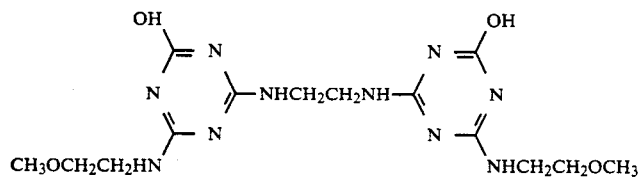

are obtained in form of white crystalline powder having a m.p. higher than 300° C.

EXAMPLE 3

In the same 2 liter apparatus of example 1, 600 cc of methyl alcohol, 80 cc of water and 100.8 g of sodium bicarbonate are introduced.

The mixture is cooled to 10° C. and 110.7 g of the cyanuric acid chloride are introduced. The temperature is allowed to raise up to 30° C. and is maintained at this value for about one hour, until the carbon dioxide release is completed.

The exothermicity of the reaction is sufficient to maintain the desired temperature.

The whole is cooled to 5° C. and then 700 cc of cold water added. The formed product is filtered and washed on the filter with cold water.

By drying the cake in oven under vacuum at 50° C., 92.1 g. of the intermediate (XXIV):

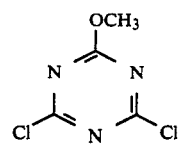 (XXIV)

are obtained in form of white crystalline powder; m.p.=90°–92° C. and chlorine content equal to 39.27% (theor.: 39.44%).

In a 1 liter reator equipped as the preceding one, 500 cc of methylene chloride and 90 g of the intermediate (XXIV) are introduced.

The mixture is cooled from the outside to 0°–2° C. and within 2 hours, 43.2 g of morpholine are introduced.

Subsequently, always at 0°–2° C. and within 3 hours, 20 g of sodium hydroxide dissolved in 70 cc of water are introduced.

After having maintained the mixture under agitation for one hour further, the aqueous phase is separated.

By distilling the methylene chloride, 112.8 g of the intermediate (XXV):

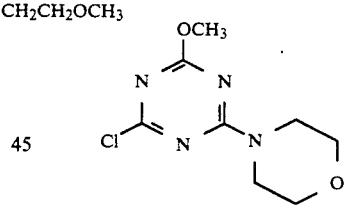 (XXV)

are obtained in form of white crystalline powder; m.p.=107°–108° C.; chlorine content 15.28% (theor.: 15.40%).

The structure of intermediates (XXIV) and (XXV) has been further confirmed by IR spectroscopic analysis.

In the same 1 liter reactor 500 cc of acetonitrile, 69.2 g of the intermediate (XXV) and 10.3 g of diethyltriamine are introduced.

The mass is heated at 80° C. and within about 4 hours 31.8 g of sodium carbonate dissolved in 100 cc of water are introduced.

The whole is kept under reflux for 8 hours and thereafter the solvent is evaporated and 500 cc of water are added.

After having kept under agitation for 30 minutes the product formed is filtered and washed on the filter with water.

By drying the cake in oven at 100° C., 61.2 g of the product:

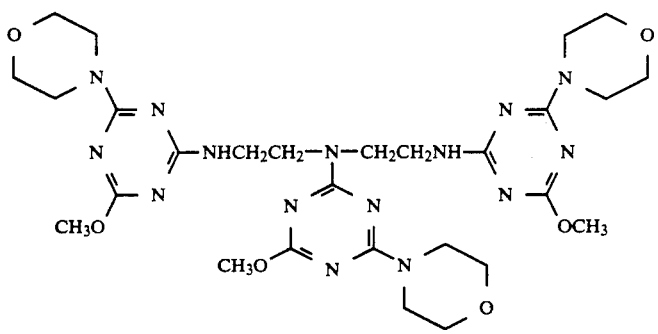

are obtained in form of white crystalline powder; M.P.=212°-214° C.

EXAMPLE 4

In a 0.5 liter reactor, equipped as in the preceding example, 250 cc of water, 54.8 g of the product of Example 3 and 47.3 g of a 37% by weight hydrochloric acid solution are introduced.

After heating to boiling the whole is maintained under reflux for 15 hours.

The whole is cooled to room temperature and 40.3 g of sodium bicarbonate are added.

Thereafter the product formed is filtered and washed on the filter with water.

By drying the cake in oven at 100° C., 46. 9 g of the product:

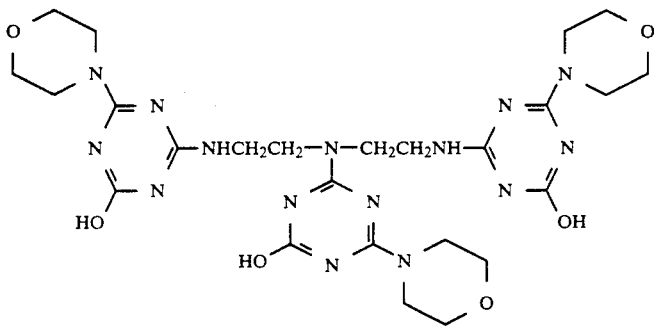

are obtained in form of white crystalline powder having m.p.=284°-286° C.

EXAMPLE 5

In a 1 liter reactor equipped as in the preceding examples, 600 cc of acetonitrile and 108 g of the intermediate (XXIV) are introduced.

The mixture is cooled to 5° C. and within 2 hours, 102 g of a 30% by weight of ammonia solution are fed.

The whole is kept under agitation for further one hour and then the product formed is filtered and washed on the filter with water. After drying in oven at 100° C., 84.2 g of the intermediate (XXVI):

(XXVI)

are obtained in form of white crystalline powder having m.p. higher than 300° C. and chlorine content equal to 21.96% (theor. 22.12%).

The structure of the intermediate (XXVI) has been confirmed by the IR spectroscopic analysis.

In a 2 liter reactor, equipped with stirrer, thermometer, feeding funnel, cooler and heating bath, 700 cc of acetonitrile, 80.3 g of the intermediate (XXVI) and 21.5 g of piperazine are introduced.

The mass is heated to boiling and within 4 hours a solution of 53 g of sodium carbonate in 200 cc of water is added.

The whole is kept under reflux for further 5 hours, then 350 cc of water are added allowing to cool to room temperature.

The product formed is filtered and washed on the filter with water.

By drying the cake in oven at 10° C., 83.2 g of the product:

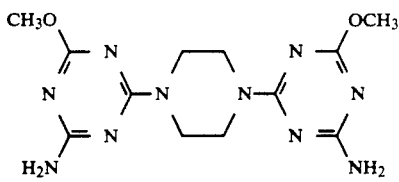

are obtained in form of white crystalline powder having m.p. higher than 300° C.

EXAMPLE 6

In the same 2 liter apparatus of example 1, 184.5 g of the cyanuric acid chloride and 1300 cc of methylene chloride are introduced.

While cooling from the outside, 87.2 g of morpholine and 40 g of sodium hydroxide dissolved in 150 g of water are contemporarily fed within 3 hours, by keeping the pH comprised between 5 and 7 and the temperature comprised between 0° and 3° C.

The whole is kept at the temperature of 0°-3° C. for further 3 hours and thereafter the aqueous phase is separated.

By distilling the methylene chloride, 230 g of the intermediate (XXVII):

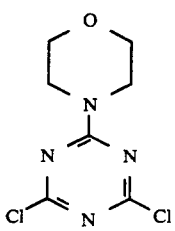

(XXVII)

are obtained in form of a white crystalline powder; m.p.=155°-157° C.; chlorine content 30.12% (theor.: 30.21%).

In the same 2 liter reactor, but equipped with heating bath, 800 cc of xylene, 141 g of the intermediate (XXVII) and 25.8 g of piperazine are introduced.

The mixture is heated at 60° C. and within 3 hours 24 g of sodium hydroxide in 100 cc of water are added.

The mixture is kept under agitation at 60° C. for 3 hours more and thereafter is cooled to room temperature.

The product formed is filtered and the cake is washed with copious amounts of water.

By drying the cake in oven at 100° C., 126.4 g of the intermediate (XXVIII):

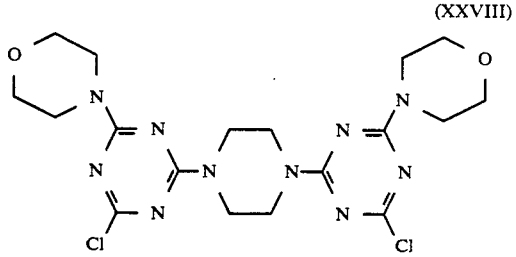

(XXVIII)

are obtained in form of white crystalline powder having a m.p. higher than 300° C. and chlorine content equal to 14.56% (theor.: 14.7%).

Structures of intermediates (XXVII) and (XXVIII) are further confirmed by IR spectroscopic analysis.

In a 1 liter reactor, equipped as above described, 500 cc of methyl alcohol are introduced and while keeping the temperature at 15°-20° C., also 17.6 g of sodium hydroxide.

The mixture is maintained under agitation until the solution is completed; thereafter 96.6 g of the intermediate (XXVIII) are introduced.

The mixture is heated to boiling and is kept under reflux for about 10 hours.

Then most of the solvent is then distilled off (about 400 cc) and the residue of the distillation is treated with 300 cc of water.

The product formed is filtered and washed on the filter with water.

By drying the cake in oven at 100° C., 87.4 g of the product:

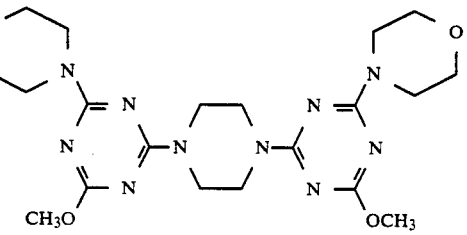

are obtained in form of white crystalline powder; m.p.=268°-270° C.

EXAMPLE 7

In the same 2 liter reactor of the preceding examples, 500 cc of acetone and 300 cc of water are introduced.

By cooling from the outside to the temperature of 0°-5° C., 110.7 g of cyanuric acid chloride are first fed. Thereafter, within 2 hours, 29.2 g of tris(2-aminoethyl)amine dissolved in 100 cc of water is added.

The mixture is maintained for a further one hour at 5° C. and thereafter, within one hour, and while keeping the temperature at 5°-7° C., 50.4 g of sodium bicarbonate are fed.

The whole is kept under agitation for further 3 hours at 7°-10° C. Then the mass is heated at 35° C. and at this temperature 61.8 g of thiomorpholine dissolved in 100 cc of water are fed within one hour.

The temperature is raised again to 40°-45° C. and a solution consisting of 24 g of sodium hydroxide in 50 cc of water is added within about 2 hours. The whole is kept for further 2 hours under agitation and then the acetone is distilled off.

The mass remaining after the distillation of the solvent is transferred to a 1 liter steel reactor and is added with 26.4 g of sodium hydroxide.

The mass is then heated to 140° C. and maintained at this temperature for about 12 hours.

At the end, the mass is cooled to room temperature, the product formed is filtered and washed on the filter with water.

By drying the cake in oven at 100° C., 132.8 g of the product:

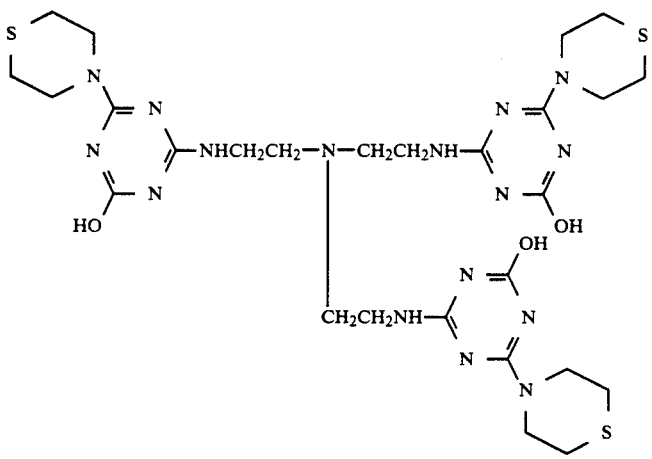

are obtained in form of white crystalline powder; m.p.=237°–239° C.

EXAMPLES 8–34

By working under conditions analogous to those described in examples from 1 to 7, products of general formula (I) reported in Table 2 are prepared. In these structures $R_3$, if present, is replaced by the triazine ring of the formula:

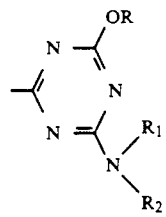

TABLE 2

| Example No. | R | $R_1$—N—$R_2$ | | $-Z-[N(-Z_1)-[Z_2]_a-]_b$ | m.p. (°C.) |
|---|---|---|---|---|---|
| 8 | H | t-$C_4H_9$ | H | —N(piperazine)N— | >300 |
| 9 | H | $(CH_2)_5OH$ | H | —HN—$(CH_2)_6$—NH— | >300 |
| 10 | n-$C_4H_9$ | —N(morpholine)O | | —N(piperazine)N— | 252–255 |
| 11 | H | —N(piperidine) | | —HN—$(CH_2)_3$—NH— | >300 |
| 12 | $CH_2CH_2N$(morpholine)O | $CH_2CH_2OH$ | H | —N(piperazine)N— | 224–227 |
| 13 | H | $CH_2CH_2OCH=CH_2$ | H | —HNCH$_2$—(cyclohexyl)—CH$_2$NH— | >300 |
| 14 | $CH_2CH_2OCH_3$ | H | H | —N(piperazine)N— | >300 |

TABLE 2-continued

| Example No. | R | R₁—N—R₂ | $-Z\left[\begin{array}{c}N-Z_1\\ [Z_2]_a\end{array}\right]_b$ | m.p. (°C.) |
|---|---|---|---|---|
| 15 | H | —N⟨piperazine⟩NH | —HN—(CH₂)₃—N(—)—(CH₂)₃—NH— | 261–264 |
| 16 | H | —N⟨morpholine⟩O | —HN—(CH₂CH₂O)₂CH₂CH₂NH— | 214–219 |
| 17 | CH₂—CH=CH₂ | CH₂CH₂OH, H | —HNCH₂CH₂NH— | 191–194 |
| 18 | H | CH₂CH₂CH₂N⟨morpholine⟩, H | —N⟨piperazine⟩N— | >300 |
| 19 | ⟨phenyl⟩ | —N⟨morpholine⟩O | —HNCH₂CH₂NH— | 232–235 |
| 20 | H | CH₂—CH=CH₂, H | —HN(CH₂)₃N⟨piperazine⟩N(CH₂)₃NH— | 277–280 |
| 21 | H | (CH₂)₂O(CH₂)₂OH, H | —N⟨piperazine⟩N— | >300 |
| 22 | H | CH₂CH₂OH, H | —HN—(CH₂)₂—[N(—)—(CH₂)₂—]₃NH— | 198–201 |
| 23 | H | —N⟨morpholine⟩O | —HN—⟨C₆H₄⟩—NH— | >300 |
| 24 | H | CH₂CH₂CH₂OCH₃, H | —N(CH₂CH₂OH)—CH₂CH₂—NH— | >300 |
| 25 | H | CH₂CH₂OH, CH₃ | —HN—⟨C₆H₄⟩—COHN—⟨C₆H₄⟩—NH— | >300 |
| 26 | H | CH₂CHCH₃, H ; OH | —HN—C(CH₃)₂—⟨C₆H₁₀⟩—C(CH₃)(NH—) | >300 |
| 27 | H | —N⟨morpholine⟩O | —HN—CH₂CH₂—N(H)—CH₂CH₂—NH— | >300 |
| 28 | H | t-C₈H₁₇, H | —N⟨piperazine⟩N— | 292–296 |

TABLE 2-continued

| Example No. | R | $R_1-N-R_2$ | $-Z-[N(-Z_1)([Z_2]_a)]_b-$ | m.p. (°C.) |
|---|---|---|---|---|
| 29 | H | cyclohexyl, H | $-HNCH_2CH_2NH-$ | >300 |
| 30 | CH$_3$ | H, H | $-HN-CH_2CH_2-N(-)-CH_2CH_2-NH-$ | 224–226 |
| 31 | H | H, H | $-N\underset{\diagdown\_\_\diagup}{\diagup^{\frown}\diagdown}N-$ (piperazine) | >300 |
| 32 | H | morpholino (-N(CH$_2$CH$_2$)$_2$O) | | $-N\underset{\diagdown\_\_\diagup}{\diagup^{\frown}\diagdown}N-$ | >300 |
| 33 | H | CH$_2$CH$_2$OH | CH$_2$CH$_2$OH | $-HNCH_2CH_2NH-$ | >300 |
| 34 | H | H | H | $-HN-CH_2CH_2-N(-)-CH_2CH_2-NH-$ | >300 |

TABLES 3 AND 4

Tests reported in the above mentioned tables relate to polymeric compositions containing products of general formula (I) prepared according to the preceding examples.

Specimens have been prepared in form of little plates having about 3 mm thickness by moulding mixtures of the granulated polymer and of additives in a MOORE plated press, by working for 7 minutes at a pressure of 40 kg/cm$^2$.

On the thus obtained plates the self-extinguishing level has been determined by measuring the oxygen index (L.O.I. according to the ASTM D-2863/77) in a Stanton Redcroft apparatus, and applying the "Vertical Burning test" which allows to classify the material at three levels 94 V-0, 94 V-1 and 94 V-2 according to rule UL 94 (edited by "Underwriters Laboratories'-"—USA).

In Table 3 values obtained using an isotactic polypropylene in flakes having a Melt Flow Index equal to 12 and a fraction insoluble in boiling n-heptane equal to 96% by weight are reported.

In Table 4 values are reported, which were obtained using a low density polyethylene in granules having a Melt Flow Index equal to 7; a granulated polystyrene containing 5% by weight of butadiene rubber and having a Melt Flow Index equal to 9; a thermoplastic polyurethane, both polyester (ESTANE 54600 ® by Goodrich) and polyether (ESTANE 58300 ® by Goodrich) in granules having specific gravity equal to 1.19 and 1.10 g/cm: respectively; an ethylene-propylene elastomeric copolymer having a percentage content by weight of propylene equal to 45; an acrylonitrile-butadiene-styrene terpolymer having specific gravity equal to 1.06 g/cm$^3$, Melt Flow Index equal to 1.6 and containing about 40% of acrylonitrile and styrene and 20% of butadiene.

TABLE 3

| Example No. | Product Example No. | parts by weight | | | | L.O.I. (ASTM D2863) | UL 94 3 mm |
|---|---|---|---|---|---|---|---|
| | | Product | PP (1) | AO (2) | APP (1) | | |
| 35 | 1 | 7.1 | 74 | 1 | 17.9 | 32.8 | V0 |
| 36 | 2 | 4.2 | 77 | 1 | 17.8 | 32.0 | V0 |
| 37 | 3 | 6.0 | 75 | 1 | 18.0 | 31.6 | V0 |
| 38 | 4 | 6.8 | 75 | 1 | 17.2 | 33.0 | V0 |
| 39 | 5 | 6.0 | 75 | 1 | 18.0 | 32.2 | V0 |
| 40 | 6 | 6.8 | 75 | 1 | 17.2 | 34.3 | V0 |
| 41 | 7 | 6.0 | 72 | 1 | 19.0 | 35.2 | V0 |
| 42 | 8 | 6.0 | 75 | 1 | 18.0 | 30.9 | V1 |
| 43 | 9 | 7.5 | 73 | 1 | 18.5 | 32.4 | V0 |
| 44 | 10 | 7.5 | 73 | 1 | 18.5 | 32.2 | V1 |
| 45 | 11 | 7.0 | 71 | 1 | 21.0 | 32.0 | V0 |
| 46 | 13 | 8.2 | 72 | 1 | 18.8 | 33.2 | V0 |
| 47 | 14 | 8.0 | 71 | 1 | 20.0 | 34.3 | V0 |
| 48 | 15 | 6.8 | 75 | 1 | 17.2 | 34.0 | V0 |
| 49 | 17 | 8.2 | 71 | 1 | 19.8 | 32.4 | V0 |
| 50 | 19 | 8.0 | 73 | 1 | 18.0 | 31.9 | V1 |
| 51 | 20 | 8.3 | 71 | 1 | 19.7 | 33.8 | V0 |
| 52 | 22 | 7.0 | 72 | 1 | 20.0 | 35.6 | V0 |
| 53 | 26 | 9.0 | 72 | 1 | 18.0 | 34.0 | V0 |
| 54 | 27 | 8.5 | 74 | 1 | 16.5 | 34.8 | V0 |
| 55 | 30 | 7.2 | 73 | 1 | 18.8 | 32.9 | V0 |
| 56 | 31 | 16.0 | 75 | 1 | 8.0 | 31.8 | V1 |
| 57 | 31 | 6.8 | 75 | 1 | 17.2 | 37.5 | V0 |
| 58 | 34 | 6.8 | 75 | 1 | 17.2 | 32.7 | V0 |
| 59 | 2 | 6.8 | 75 | 1 | 17.2* | 36.2 | V0 |
| 60 | 4 | 6.8 | 72 | 1 | 20.2 | 34.2 | V0 |
| 61 | 31 | 6.5 | 73 | 1 | 19.5* | 37.8 | V0 |
| 62 | 2 | 6.3 | 74 | 1 | 18.7(3) | 34.2 | V0 |
| 63 | 5 | 6.8 | 75 | 1 | 17.2(4) | 30.9 | V0 |

(1) PP = Polypropylene
APP = ammonium polyphosphate-Exolit 422$^R$ (Hoechst)
*APP = microincapsulated with melamine-formaldehyde resin Exolit 462$^R$ (Hoechst)
(2) AO = antioxidant mixture consisting of 2 parts of dilaurylthiopropionate and 1 part of tetra[3-(3,5-di-terbutyl-4-hydroxyphenyl)propionate] of pentaerythritol.
(3) ammonium salt from 1-aminoethane-1,1-diphosphonic acid.
(4) ammonium salt from 1-hydroxyethane-1,1-diphosphonic acid.

TABLE 4

| Example No. | Polymeric Supp. 1 | Product Example No. | parts by weight Product | Polymer | AO (2) | APP (1) | L.O.I. (ASTM-D2863) | UL 94 3 mm |
|---|---|---|---|---|---|---|---|---|
| 64 | LDPE | 1 | 7.2 | 70 | 1 | 21.8 | 30.3 | V1 |
| 65 |  | 2 | 7.8 | 68 | 1 | 23.2 | 33.7 | V0 |
| 66 |  | 21 | 8.5 | 65 | 1 | 25.5 | 32.4 | V0 |
| 67 |  | 22 | 9.0 | 60 | 1 | 30.0 | 38.9 | V0 |
| 68 |  | 27 | 7.8 | 70 | 1 | 21.2 | 32.1 | V0 |
| 69 | HIPS | 1 | 20.0 | 60 | 1 | 19.0 | 33.2 | V0 |
| 70 |  | 21 | 10.0 | 65 | 1 | 24.0 | 32.0 | V0 |
| 71 |  | 31 | 10.2 | 68 | 1 | 20.8 | 31.4 | V0 |
| 72 | PP/PE | 2 | 9.7 | 65 | 1 | 24.3 | 34.3 | V0 |
| 73 |  | 4 | 7.3 | 70 | 1 | 21.7 | 33.9 | V0 |
| 74 |  | 24 | 8.5 | 65 | 1 | 25.5 | 34.1 | V0 |
| 75 | PU (ester) | 2 | 8.3 | 70 | 1 | 20.7 | 33.6 | V0 |
| 76 |  | 4 | 7.2 | 70 | 1 | 21.8 | 35.0 | V0 |
| 77 |  | 33 | 8.3 | 70 | 1 | 20.7 | 34.3 | V0 |
| 78 | PU (ether) | 4 | 8.3 | 66 | 1 | 24.7 | 31.7 | V0 |
| 79 | ABS | 2 | 12.8 | 67 | 1 | 19.2 | 30.4 | V0 |
| 80 |  | 24 | 7.8 | 68 | 1 | 23.2 | 31.6 | V0 |

(1) APP = ammonium polyphosphate-Exolit 422$^R$ (Hoechst)
LDPE = low density polyethylene
HIPS = polystyrene containing 5% of butadiene rubber
PU (ester) = polyurethane polyester
PU (ether) = polyurethane polyether
PP/PP = propylene-ethylene copolymer
ABS = acrylonitrile-butadiene-styrene terpolymer
(2) AO = antioxidizing agent
Mixture consisting of 2 parts of dilaurylpropionate and 1 part of tetra [3-(3,5-di-terbutyl-4-hydroxyphenyl)-propionate] of pentaerythritol.

EXAMPLE 81 (COMPARISON EXAMPLE)

By working according to the modalities used in examples from 35 to 63, but using as nitrogenous compound the 2,4-diamino-6-hydroxy-1,3,5-triazine, the composition specified hereinafter is prepared:

| | |
|---|---|
| Polypropylene | 72 parts by weight |
| Antioxidant | 1 part by weight |
| Ammonium polyphosphate | 19.3 parts by weight |
| 2,4-diamino-6-hydroxy-1,3,5-triazine | 7.7 parts by weight |

Using the above mentioned composition specimens have been prepared which have been subjected to self-extinguishing tests according to the previously described modalities.

The following results have been obtained: L.O.I.=23.8

UL 94 (3 mm): class B (the specimen burns).

What is claimed as new and desired to be secured by Letters Patent of the United States is:

1. Self-extinguishing polymeric compositions comprising:
a) from 90 to 40 parts by weight of a thermoplastic polymer or of a polymer showing elastomeric properties;
b) from 6 to 33 parts by weight of one or more phosphates and/or phosphonates of ammonium or of an amine;
c) from 3 to 27 parts by weight of one or more polycondensed compounds derived from 2,4-diamino-6-hydroxy-1,3,-5-triazine, having the formula (I):

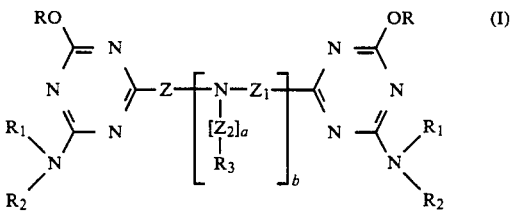

wherein:
R = H; $+C_nH_{2n}+Y$ wherein
n is an integer comprised between 1 and 8;
Y is H; CN; —O—$(C_1-C_4)$-alkyl; —O—$(C_2-C_4)$-alkenyl; $(C_6-C_{12})$-cycloalkyl or -alkylcycloalkyl; —O—$(C_6-C_{12})$-aryl;

wherein radicals $R_4$, which may be the same or different, are: $(C_1-C_4)$-alkyl or $(C_3-C_4)$-alkenyl or the group:

is replaced by a heterocyclic radical selected from the group consisting of pyrrolidine, piperidine, morpholine, thiomorpholine, piperazine, 4-methylpiperazine, or 4-ethylpiperazine, said heterocyclic radical being bound to the alkyl chain through a nitrogen atom;

($C_2$-$C_6$)-alkenyl; ($C_6$-$C_{12}$)-cycloalkyl or -alkylcycloalkyl; ($C_6$-$C_{12}$)-aryl or -aralkyl;

radicals $R_1$ and $R_2$, which may be the same or different and which can have different meanings on each triazine ring, are:

H; ($C_1$-$C_{18}$)-alkyl; ($C_2$-$C_8$)-alkenyl; ($C_6$-$C_{16}$)-cycloalkyl or -alkylcycloalkyl;

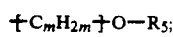

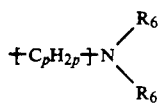

with:

m = integer comprised between 2 and 8;
p = integer comprised between 2 and 6;
$R_5$ = H; ($C_1$-$C_8$)-alkyl, preferably H or ($C_1$-$C_4$)-alkyl; ($C_2$-$C_6$)-alkenyl;
—O—$R_7$ wherein q is an integer comprised between 1 and 4 and $R_7$ is H or ($C_1$-$C_4$)-alkyl; ($C_6$-$C_{12}$)-cycloalkyl or -alkylcycloalkyl;

radicals $R_6$, which may be the same or different, are:
H; ($C_1$-$C_8$)-alkyl; ($C_2$-$C_6$)-alkenyl; ($C_6$-$C_{12}$)-cycloalkyl or -alkylcycloalkyl; ($C_1$-$C_4$)-hydroxyalkyl;

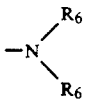

is replaced by a heterocyclic radical selected from the group consisting of aziridine, pyrrolidine, piperidine, morpholine, thiomorpholine, piperazine, 4-methylpiperazine, or 4-ethylpiperazine, said heterocyclic radical being bound to the alkyl chain through the nitrogen atom; or in the formula (I) the group:

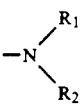

is replaced by a heterocyclic radical selected from the group consisting of aziridine, pyrrolidine, piperidine, morpholine, thiomorpholine, piperazine, 4-methylpiperazine, 4-ethylpiperazine, 2-methylpiperazine, or 2,5-dimethylpiperazine, said heterocyclic radical being bound to the triazinic ring through a nitrogen atom;

a is 0 or 1;
b is 0 or an integer comprised between 1 and 5;
$R_3$ is hydrogen or:

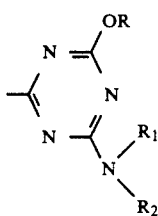

and its meaning may vary within each repeating unit;

when b is 0, Z is a divalent radical comprised in one of the following formulas:

(II)

wherein radicals $R_8$, which may be the same or different, are hydrogen or ($C_1$-$C_4$)-alkyl;

(III)

(IV)

wherein r is an integer comprised between 2 and 14; $R_9$ is hydrogen; ($C_1$-$C_4$)-alkyl; ($C_2$-$C_6$)-alkenyl; ($C_1$-$C_4$)-hydroxyalkyl;

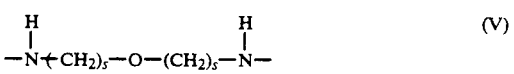

(V)

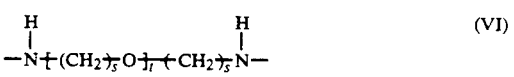

(VI)

wherein s is an integer comprised between 2 and 5 and t is an integer comprised between 1 and 3;

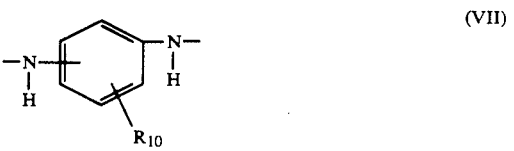

(VII)

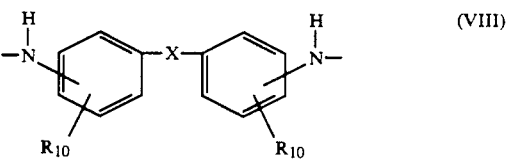

(VIII)

wherein:
X is C—C; O; S; S—S; SO; $SO_2$; NH; $NHSO_2$; NHCO; N=N; $CH_2$; $R_{10}$ is hydrogen; hydroxy; ($C_1$-$C_4$)-alkyl; ($C_1$-$C_4$)-alkoxy;

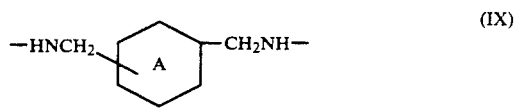

(IX)

wherein A may be either a saturated or an unsaturated ring;

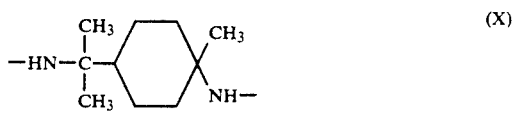

(X)

-continued

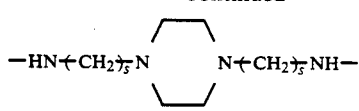  (XI)

wherein s has the previously defined meaning;
when on the contrary b is an integer comprised between 1 and 5 the group:

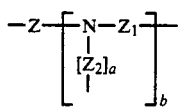

is a polyvalent radical comprised in one of the following formulas:

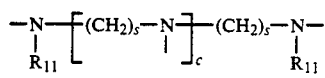  (XII)

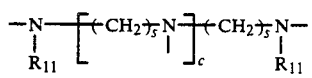  (XII)

wherein:
$R_{11}$ is hydrogen or ($C_1$–$C_4$)-alkyl;
c is an integer comprised between 1 and 5;
indexes s, which may be the same or different, have the meaning previously defined;

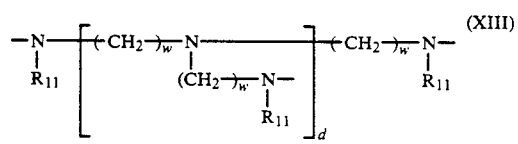  (XIII)

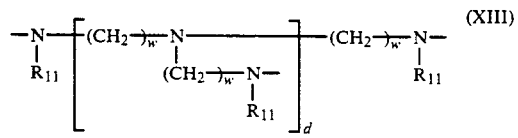  (XIII)

wherein:
$R_{11}$ has the previously defined meaning;
w is an integer comprised between 2 and 4;
d is 1 or 2.

2. Self-extinguishing polymeric compositions according to claim 1, wherein the group:

in formula (I) is replaced by heterocyclic radicals selected from the group consisting of aziridine, pyrrolidine, piperidine, morpholine, thiomorpholine, piperazine, 4-methylpiperazine, 4-ethylpiperazine, 2-methypiperazine, 2,5-dimethylpiperazine, 2,3,5,6-tetramethylpiperazine, 2,2,5,5-tetramethylpiperazine, 2-ethylpiperazine, or 2,5-diethylpiperazine.

3. Self-extinguishing polymeric compositions according to claim 1, wherein at least one of radicals from $R_1$ or $R_2$ in the formula (I) is replaced by a group:

wherein:
m is an integer comprised between 2 and 4 and
$R_5$ is hydrogen or ($C_1$–$C_4$)-alkyl.

4. Self-extinguishing polymeric compositions as in claim 1, wherein the group:

is replaced by a heterocyclic radical selected from the group consisting of pyrrolidine, piperidine, morpholine, thiomorpholine, piperazine, 4-methylpiperazine, or 4-ethylpiperazine.

5. Self-extinguishing polymer compositions as in claim 1, wherein the group:

is replaced by a heterocyclic radical selected from the group consisting of aziridine, pyrrolidine, piperidine morpholine, thiomorpholine, piperazine, 4-methylpiperazine, or 4-ethylpiperazine.

6. Self-extinguishing polymeric compositions as in claim 1, wherein R, in the formula (I) is hydrogen.

7. Self-extinguishing polymeric compositions as in claim 1, wherein R, in the formula (I) is replaced by a group:

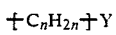

wherein:
n is an integer comprised between 1 and 4 and
Y is hydrogen.

8. Self-extinguishing polymeric compositions as in claim 1, wherein the ammonium phosphate or phosphates (b) have the formula $(NH_4)_{n+2}P_nO_{3n+1}$ wherein n is an integer equal to or higher than 2.

9. Self-extinguishing polymeric compositions as in claim 1, wherein the ammonium phosphate or phosphates (b) have the general formula $(NH_4PO_3)_n$ wherein n is an integer comprised between 50 and 500.

10. Self-extinguishing polymeric compositions as in claim 1, wherein the phosphate or phosphates of amine (b) are selected from the dimethylammonium or diethylammonium phosphate; ethylenediamine phosphate; melamine ortho- or pyrophosphate.

11. Self-extinguishing polymeric compositions as in claim 1, wherein the ammonium phosphonate or phosphonates (b) are those mono and polysubstituted selected from salts derived from mono and polyphosphonic acids.

12. Self-extinguishing polymeric compositions as in claim 1, wherein the polymer (a) is selected from olefin polymers and copolymers of general formula R—CH=$CH_2$ wherein R is a hydrogen atom or a ($C_1$–$C_8$)-alkyl or -aryl radical; acrylonitrile/- butadiene/styrene (ABS) copolymers; styrene/acrylonitrile (SAN) copolymers; polyurethane; polyethyleneterphthalate; polybutyleneterphthalate; polyamides.

13. Self-extinguishing polymeric compositions according to claim 12, wherein the olefin polymers and copolymers are selected from:
  (i) isotactic or prevailing isotactic polypropylene;
  (ii) HDPE, LLDPE, LDPE polyethylene;
  (iii) propylene crystalline copolymers with lower proportions of ethylene and/or other alpha-olefins, such as 1-butene, 1-hexene, 1-octene, 4-methyl-1-pentene;
  (iv) heterophasic compositions comprising (A) a homopolymeric fraction of propylene or one of copolymers described under item (3) and (B) a copolymeric fraction consisting of elastomeric copolymers of ethylene with an alpha-olefin, optionally containing lower proportions of a diene, wherein the alpha-olefin is preferably selected from propylene and 1-butene;
  (v) elastomeric copolymers of ethylene with alpha-olefins optionally containing lower proportions of a diene.

14. Molded articles, containing a composition as in any one of claim 1-3.

* * * * *